United States Patent [19]
Odorisio et al.

[11] Patent Number: 6,103,938
[45] Date of Patent: Aug. 15, 2000

[54] PROCESS FOR PREPARING 4-(SUBSTITUTED PHENYL)-3,4-DIHYDRO-2H-NAPHTHALEN-1-ONES

[75] Inventors: Paul A. Odorisio, Leonia, N.J.; Stephen D. Pastor, Danbury, Conn.; Sai P. Shum, Hightstown, N.J.

[73] Assignee: Ciba Specialty Chemicals Corporation, Tarrytown, N.Y.

[21] Appl. No.: 09/259,720

[22] Filed: Mar. 1, 1999

Related U.S. Application Data

[60] Provisional application No. 60/082,812, Apr. 23, 1998.

[51] Int. Cl.$^7$ .................................................. C07C 45/45
[52] U.S. Cl. .......................... 568/322; 568/319; 568/323
[58] Field of Search .................................... 568/322, 323, 568/319

[56] References Cited

U.S. PATENT DOCUMENTS

| | | | |
|---|---|---|---|
| 4,839,104 | 6/1989 | Quallich et al. | 26/396 |
| 5,019,655 | 5/1991 | Adrian | 568/322 |
| 5,196,607 | 3/1993 | Quallich | 568/327 |
| 5,466,880 | 11/1995 | Quallich | 568/319 |

FOREIGN PATENT DOCUMENTS

95/15299  6/1995  WIPO.

*Primary Examiner*—Sreeni Padmanabhan
*Attorney, Agent, or Firm*—Luther A. R. Hall

[57] ABSTRACT

4-(Substituted phenyl)-3,4-dihydro-2H-naphthalen-1-ones, which are useful as intermediates in the preparation of antidepressant agents, are conveniently prepared by reacting 1-substituted naphthalenes and an aromatic moiety in the presence of an acid catalyst. 4-(3,4-Dichlorophenyl)-3,4-dihydro-2H-naphthalen-1-one, which is useful as an intermediate in the preparation of the antidepressant sertraline, is conveniently prepared by reacting 1-naphthyl acetate and o-dichlorobenzene in the presence of an acid catalyst.

11 Claims, No Drawings

PROCESS FOR PREPARING 4-(SUBSTITUTED PHENYL)-3,4-DIHYDRO-2H-NAPHTHALEN-1-ONES

This application claims the benefit under 35 USC 119(e) of U.S. Provisional Application No. 60/082,812, filed on Apr. 23, 1998.

The instant invention pertains to a new process for the preparation of 4-(substituted phenyl)-3,4-dihydro-2H-naphthalen-1 ones by reacting substituted naphthalenes and benzene, chlorobenzene or o-dichlorobenzene in the presence of an acid catalyst.

BACKGROUND OF THE INVENTION

U.S. Pat. Nos. 4,839,104; 5,019,655; 5,196,607 and 5,466,880 as well as WO95/15299 describe various methods and processes for preparing 4-(3,4-dichlorophenyl)-3,4-dihydro-2H-naphthalen-1-one. None of these prior art patents describe or suggest the new instant process for the preparation of this valuable intermediate for the preparation of the antidepressant sertraline which is cis-(1S)(4S)-N-methyl-4-(3,4-dichlorophenyl)-1,2,3,4-tetrahydro-1-naphthaleneamine.

The instant process has the advantage of using a readily accessible and relatively inexpensive intermediate 1-naphthyl acetate which has high solubility in o-chlorobenzene.

DETAILED DISCLOSURE

The new instant process for preparing 4-(substituted phenyl)-3,4-dihydro-2H-naphthalen-1-ones follows the scheme outlined below:

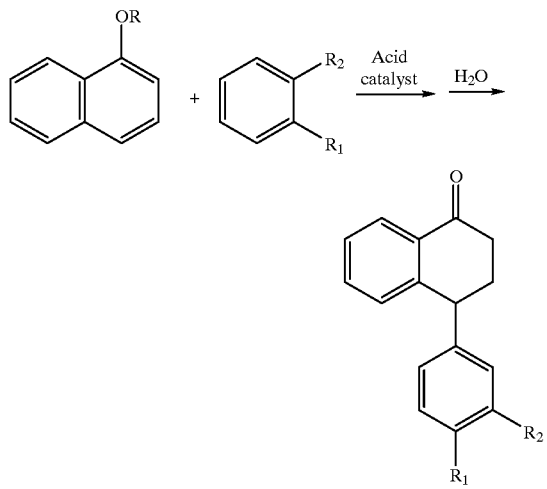

wherein

R is —CO—$R_3$ or —Si($CH_3$)$_3$, $R_3$ is alkyl of 1 to 6 carbon atoms or phenyl, and $R_1$ and $R_2$ are independently hydrogen or chloro.

Preferably, $R_3$ is methyl, and $R_1$ and $R_2$ are both chloro.

More particularly, the preferred instant process is outlined below:

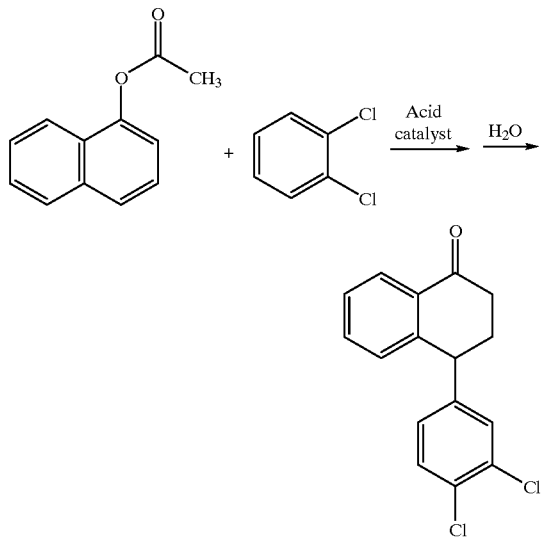

Preferably, the acid catalyst used in this general process is aluminum bromide or aluminum chloride, most preferably aluminum chloride.

Preferably, the amount of acid catalyst is from one molar equivalent to five molar equivalents based on the 1-substituted naphthalene, preferably 1-naphthyl acetate or 1-naphthyl benzoate, reactant.

Preferably, the catalyst is either aluminum bromide or aluminum chloride used in a quantity of from one molar equivalent to 2.2 molar equivalents based on the 1-substituted naphthalene, preferably 1-naphthyl acetate.

The following Examples are for illustrative purposes only and are not to be construed as limiting the instant invention in any manner whatsoever.

EXAMPLE 1

Into a solution of 9.3 g (0.05 mole) of 1-naphthyl acetate in 70 mL of o-dichlorobenzene at ambient temperature is added 14.7 g (0.11 mole) of aluminum chloride. The resulting reaction mass is then heated to 60–70° C. After two hours, inspection of the $^1$HNMR spectrum of an aliquot finds complete disappearance of the starting 1-naphthyl acetate. The reaction mass is then cooled to ambient temperature and poured into 100 mL of water at 0° to 5° C. The resultant mixture is allowed to warm to ambient temperature and is stirred for one hour. The layers are separated and the lower organic layer is dried over anhydrous sodium sulfate. The excess o-dichlorobenzene is recovered by distillation under reduced pressure to yield 13.4 g of a viscous oil residue. The reaction residue contains 22% of 4-(3,4-dichlorophenyl)-3,4-dihydro-2H-naphthalen-1-one based on GC analysis.

EXAMPLE 2

Into a suspension of 6.7 g(0.05 mole) of aluminum chloride in 45 mL of o-dichlorobenzene heated to 70° C. is added dropwise a solution of 9.3 g (0.05 mole) of 1-naphthyl acetate in 25 mL of o-dichlorobenzene. The addition requires one hour. The reaction temperature is maintained at 60–70° C. with external heating. After three hours from the completion of the addition period, inspection of the $^1$HNMR spectrum of an aliquot finds complete disappearance of the starting 1-naphthyl acetate. Some 10.2 g of the reaction product is isolated as described in Example 1. The reaction product contains 2.4% of 4-(3,4-dichlorophenyl)-3,4-dihydro-2H-naphthalen-1-one based on GC analysis.

EXAMPLE 3

Into a suspension of 4.6 g (17 mmol) of aluminum bromide in 5 mL of o-dichlorobenzene at ambient temperature is added dropwise a solution of 1.69 g(8.6 mmol) of 1-naphthyl acetate in 7 mL of o-dichlorobenzene. After heating at 50–70° C. for one hour, thin layer chromatography analysis of an aliquot finds complete disappearance of the starting 1-naphthyl acetate. Some 1.8 g of reaction product is isolated as described in Example 1. The reaction product contains 20% of 4-(3,4-dichlorophenyl)-3,4-dihydro-2H-naphthalen-1-one based on GC analysis.

EXAMPLE 4

When using the general procedure of Example 1, 1-naphthyl acetate is replaced with an equivalent amount of 1-naphthyl propionate, 1-naphthyl butyrate, 1-naphthyl valerate or 1-naphthyl caproate, the reaction residue contains 4-(3,4-dichlorophenyl)-3,4-dihydro-2H-naphthalen-1-one.

EXAMPLE 5

When using the general procedure of Example 1, 1-naphthyl acetate is replaced with an equivalent amount of 1-naphthyl benzoate or 1-trimethylsiloxynaphthalene, the reaction residue contains 4-(3,4-dichlorophenyl)-3,4-dihydro-2H-naphthalen-1-one.

EXAMPLE 6

When using the general procedure of Example 2, o-dichlorobenzene is replaced with an equivalent amount of benzene, the reaction residue contains 4-phenyl-3,4-dihydro-2H-naphthalen-1-one.

EXAMPLE 7

When using the general procedure of Example 2, o-dichlorobenzene is replaced with an equivalent amount of chlorobenzene, the reaction residue contains a mixture of 4-(3-chlorophenyl)-3,4-dihydro-2H-naphthalen-1-one and 4-(4-chlorophenyl)-3,4-dihydro-2H-naphthalen-1-one.

What is claimed is:

1. A process for the preparation of a compound of formula I

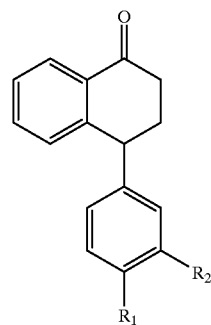

wherein $R_1$ and $R_2$ are independently hydrogen or chloro, which comprises reacting a compound of formula II

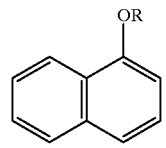

wherein

R is —CO—$R_3$ or —Si(CH$_3$)$_3$, and $R_3$ is alkyl of 1 to 6 carbon atoms or phenyl, with a compound of formula III

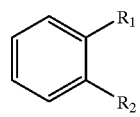

wherein $R_1$ and $R_2$ are independently hydrogen or chloro, in the presence of an effective amount of an acid catalyst to form the compound of formula I.

2. A process according to claim 1 wherein the acid catalyst is aluminum bromide or aluminum chloride.

3. A process according to claim 2 wherein the acid catalyst is aluminum chloride.

4. A process according to claim 1 wherein the acid catalyst is present in an amount from one molar equivalent to five molar equivalents based on the compound of formula II.

5. A process according to claim 4 wherein the acid catalyst is present in an amount from one molar equivalent to 2.2 molar equivalents based on the compound of formula II.

6. A process according to claim 1 wherein $R_3$ is methyl, and $R_1$ and $R_2$ are both chloro.

7. A process for the preparation of 4-(3,4-dichlorophenyl)-3,4-dihydro-2H-naphthalen-1-one of formula A (A)

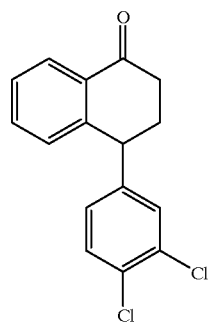

which comprises
reacting 1-naphthyl acetate of the formula B (B)

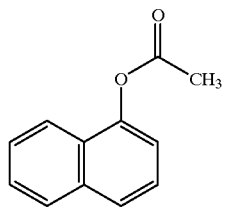

with o-dichlorobenzene of formula C (C)

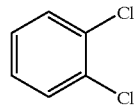

in the presence of an effective amount of an acid catalyst to form the compound of formula A.

8. A process according to claim 7 wherein the acid catalyst is aluminum bromide or aluminum chloride.

9. A process according to claim 8 wherein the acid catalyst is aluminum chloride.

10. A process according to claim 7 wherein the acid catalyst is present in an amount from one molar equivalent to five molar equivalents based on the 1-naphthyl acetate.

11. A process according to claim 10 wherein the acid catalyst is present in an amount from one molar equivalent to 2.2 molar equivalents based on the 1-naphthyl acetate.

* * * * *